United States Patent [19]

Friddle, Jr.

[11] Patent Number: 5,203,765

[45] Date of Patent: Apr. 20, 1993

[54] ADJUSTABLE HALO SYSTEM ORTHOPEDIC APPLIANCE AND METHOD

[75] Inventor: Frank E. Friddle, Jr., Honea Path, S.C.

[73] Assignee: Friddle Orthopedic Appliances, Inc., Honea Path, S.C.

[21] Appl. No.: 708,490

[22] Filed: May 31, 1991

[51] Int. Cl.$^5$ .............................................. A61F 5/00
[52] U.S. Cl. ...................................... 602/18; 602/17
[58] Field of Search .............. 128/75, 76 R, 78, 87 B, 128/DIG. 23; 606/54-59; 602/17-19

[56] References Cited

U.S. PATENT DOCUMENTS 4,648,390 3/1987 Friddle .
4,738,252 4/1988 Friddle et al. .
4,807,605 2/1989 Mattingly .

OTHER PUBLICATIONS

Durr-Fillauer Medical, Inc. brochure; 2 pages front & back; printed Sep. 1990; "MRI Compatible Halo".
Brochure entitled "Friddle MRI Halo System" by Friddle's Orthopedic Appliances, 8 pages, undated.
Brochure entitled "Kronner Halo II" by Kronner Inc., 1 page, two-sided, undated.
Brochure entitled "Halo Assemblies and Components" by Durr-Fillauer, pp. 52-54, undated.
Reprint of Article entitled "Compatibility of Cervical Spine Braces with MRI Imaging; A study of Nine Nonferrous Devices" by Clayman et al., pp. 385-390, Mar.-/Apr. 1990, Journal of American Society of Neuroradiology.
Booklet entitled "Guide to Wearing The Halo Vest" by Bremer Medical Companies, Inc., pp. 1-14, Copyright 1988.
Brochure entitled "Bremer Halo Systems" by Bremer Medical, Inc., 1 page, two-sided, undated.

Primary Examiner—Richard J. Apley
Assistant Examiner—Linda C. M. Dvorak
Attorney, Agent, or Firm—Dority & Manning

[57] ABSTRACT

A halo system orthopedic appliance includes an adjustable two poster arrangement in which the connections between the respective posts and the appliance are made with respective clamp mechanisms. Each poster is slidably received in a channel formed by each clamp. Each clamp is rotatably received on a single clamp screw which when tightened simultaneously fixes the slidably adjusted position of the post relative the clamp and the rotatably adjusted position of the clamp relative the appliance. Serrations on opposing surfaces between respectively paired clamps and adapter brackets carried on the halo ring, and respectively between two clamps and superstructure supported on a patient vest, enhances the clamping effect. During application of the appliance, the patient's skeletal process is first aligned in a desired orientation, and thereafter the four respective clamps located adjacent each end of the pair of posters are secured. The two poster arrangement and single clamp screw per clamp advantageously permits rapid alignment, adjustment, and securement of the orthopedic appliance to a patient. Relative bulk of the appliance is also reduced for imaging and aesthetic advantages.

28 Claims, 5 Drawing Sheets

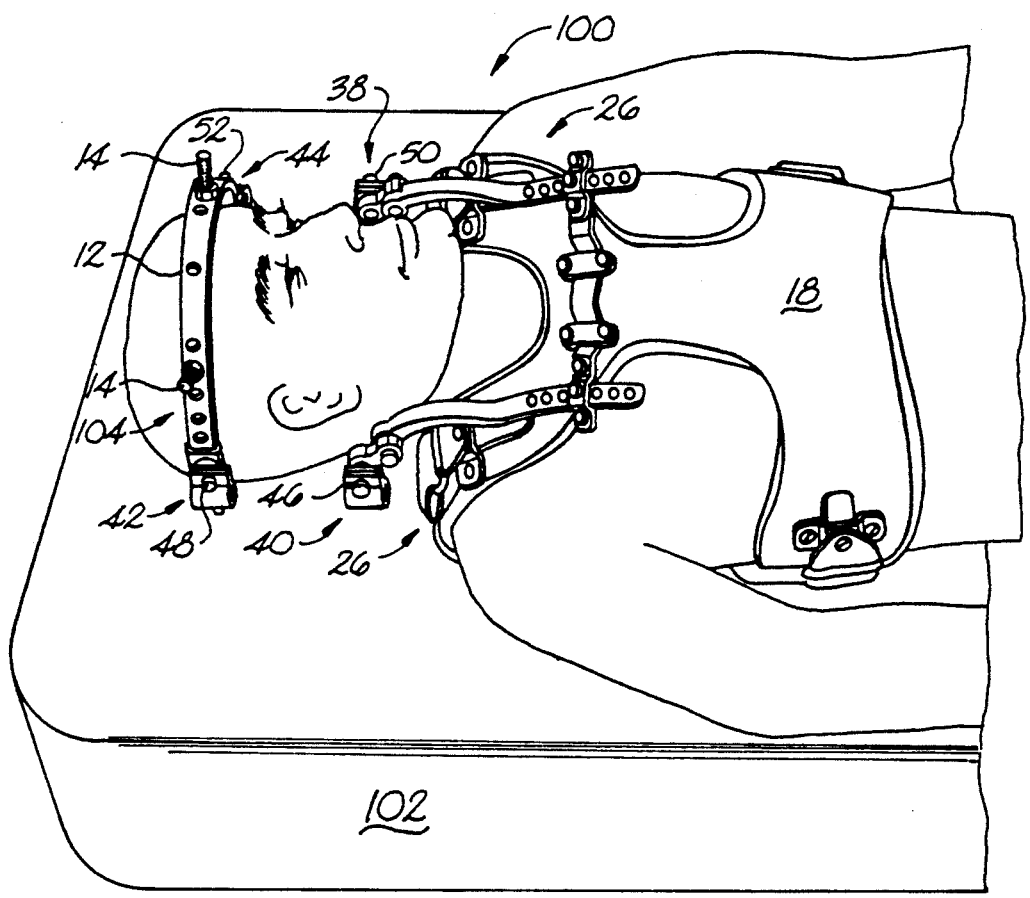
Fig. 4
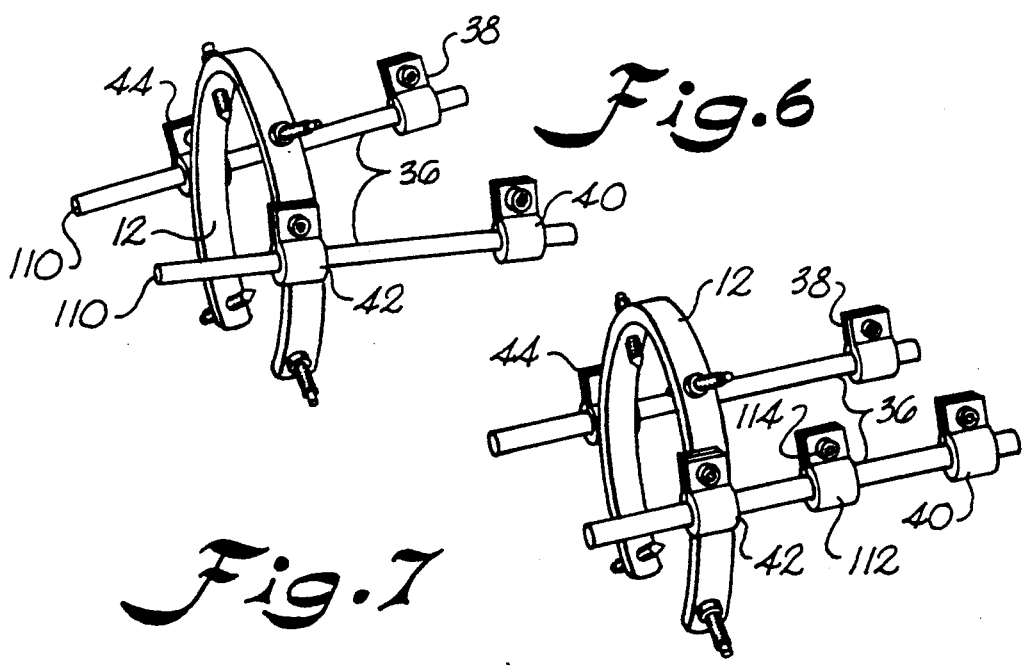
Fig. 6
Fig. 7

ADJUSTABLE HALO SYSTEM ORTHOPEDIC APPLIANCE AND METHOD

BACKGROUND OF THE INVENTION

The present invention concerns in general an improved halo system and method, and in particular concerns an improved adjustable, two poster halo system orthopedic appliance and corresponding methodology.

The treatment of orthopedic patients includes use of so-called halo-vest systems, in which a ring or halo is secured with skull pins or the like to the skull of a patient and thereafter rigidly aligned in relation to the patient's skeletal system. In general, the halo is variously interconnected to some other structure worn by the patient, such as a vest.

The general principles of operation of the halo-vest system in the treatment of injuries to the cervical spine are well known. For example, such prior art systems are frequently used to introduce a degree of traction to the cervical spine of a patient. The cervical spine is stabilized in a selected position by fixing of the skull in reference to the chest through use of some exterior mechanical apparatus. The above-mentioned traction is achieved through use of the various mechanisms interconnecting the halo and the vest. Soft tissue stresses are generally low because forces involved are spread over the chest area by the mechanical unit.

Since introduction of the halo principle generally related to orthopedic surgery during the 1950s, various systems have been provided. For example, the present assignee, Friddle Orthopedic Appliances of Honea Path, S.C., has marketed a halo system which interconnects a halo ring and halo vest with four upright turnbuckles. The base of the four turnbuckles interconnect with screws to superstructure supported on a vest. The upper ends of the four turnbuckles interconnect through screws to a pair of generally horizontal bars which in turn are connected at an upward extension thereof to the halo ring. While such a four turnbuckle design allows for infinite adjustment and provides excellent stability, a finite amount of time is required for making such adjustments, and a finite amount of space is required for the four separate turnbuckles. A serration system is also provided in connection with anterior-posterior deflection superstructure adjustment. Such further adjustability permits additional flexibility in use and adjustment of the appliance, but requires the additional time and effort to do so. Also, the adjustability of a turnbuckle system is finite.

Bremer Medical Companies, Inc., of Jacksonville, FL, markets a halo system which provides four upright posts at widely separated positions supporting a pair of transverse bars which carry respective halo clamps. Overall adjustability is limited, particularly at the base of the posts, which have curved and angled portions. Likewise, plural adjustments are necessary in order to effect changes in traction, for example, to equally raise the halo relative all four upright posts.

Various advantages and disadvantages of available systems and materials have been discussed in the literature. For example, the above-referenced Bremer Medical Companies, Inc., has an MRI compatible version of its halo system which has been the subject of a study report entitled "Compatibility of Cervical Spine Braces with MR Imaging" by Clayman the American Society of Neuroradiology. Such study also reports on a four poster design by PMT Corporation of Chanhassen, Minnesota, which uses components interconnected with plastic ball and socket joints, and which require securement of plural screws to immobilize each of the respective ball and socket joints.

Some prior systems make use of an arrangement of two upright members. For example, one halo system by Durr-Fillauer includes two turnbuckles secured by bolts at their respective ends to a halo ring and to superstructure carried on a vest. Again, the adjustability of turnbuckles is limited, and separate operations must be made in order to adjust a given turnbuckle per se verses its interconnection and relationship to either the superstructure or the halo ring. Kronner Inc. of Roseburg, OR, markets a product having two uprights. The upper end of each upright is threaded, with a traveling clamp captured along such threaded portion at a desired point by a respective pair of upper and lower jam nuts. The upper traveling members of the Kronner product each interconnect with another support member which then directly connects to the halo ring. Each lower end of an upright is secured by respective lower clamps also requiring each two bolts for adjustment and securement.

In the foregoing two upright devices, there can be a question of adequate stability and strength of the traction and alignment of the cervical spine of the patient, added with the complexity and time factor of effecting application and adjustment of the appliance.

Friddle et. al. (U.S. Pat. No. 4,738,252), commonly assigned with the subject application, relates to a mechanical joint construction in which a number of elements (shown in exploded view in FIG. 2 thereof) are assembled with a fastening bolt 56, which may be used to change or relocate the position of limited pivotable movement of the orthosis 10. One of the inventors of the '252 patent has another U.S. Pat. No. 4,648,390, entitled LOW PROFILE NECK RING ORTHOSIS, which is another example of a prior device which may be used as an attachment for supporting structure of an orthopedic body brace employed to treat curvature of the spine.

SUMMARY OF THE INVENTION

The present invention recognizes and addresses various disadvantages and shortcomings of various aspects of orthopedic appliances, particularly halo system appliances. Thus, broadly speaking, a principle object of this invention is improved orthopedic appliances. Another present general object of the invention is improved corresponding methodology relating to orthopedic appliances. More particularly, one main concern is improved adjustable, two poster halo system orthopedic appliances and corresponding methodology.

It is another more particular object of this invention to provide an improved adjustable orthopedic appliance which has excellent strength and stability in a two poster configuration. More specifically, it is a present object to obviate turnbuckle arrangements and thereby eliminate disadvantages thereof.

It is another general object of the present invention to provide improved orthopedic appliance apparatus and methodology which facilitates application of the appliance to a patient in less time than convention devices and methodology. In accordance with such object, it is a present purpose to provide simplicity in both structure and methodology, by which such advantageous time improvement may be achieved. In addition, it is desired to improve the halo-vest orthopedic treatment field generally by making possible quick and accurate application and/or adjustment of a device having a high degree of stability and strength with a low degree of patient inconvenience due to bulk of the appliance.

It is another general object of the present invention to provide apparatus and corresponding methodol which utilizes a unique clamp arrangement to virtually eliminate slippage while providing a practical and successful two poster arrangement. It is another more particular object to provide such a practical two poster arrangement which advantageously permits considerable stability and ease during application and adjustment thereof while permitting a reduction in the number of necessary steps to effect such application and adjustment.

It is yet another present object to provide an improved apparatus and methodology resulting in a less bulky arrangement, for improved aesthetics and cosmetics, for example, so as to more readily facilitate the wearing of a patient's normal clothing.

It is yet another object to provide apparatus and methodology which facilitates MRI and X-ray compatibility, both through the advantageous use of particular materials and the advantageous arrangement of present structures.

Additional objects and advantages of the invention are set forth, or will be apparent to those of ordinary skill in the art from the detailed description which follows. Also, it should be further appreciated that modifications and variations to the specifically illustrated and discussed features and steps hereof may be practiced in various embodiments and uses of this invention without departing from the spirit and scope thereof, by virtue of present reference thereto. Such variations may include, but are not limited to, substitute of equivalent means and features or materials or steps for those shown or discussed, and the functional or positional reversal of various parts, features, steps, or the like.

Still further, it is to be understood that different embodiments, as well as different presently preferred embodiments, of this invention may include various combinations or configurations of presently disclosed features or steps, or their equivalents (including combinations or configurations, or features or steps thereof not expressly shown or stated). One exemplary such embodiment of the present invention relates to an adjustable, two poster halo system orthopedic appliance. Such a present appliance comprises a halo ring carrying a plurality of skull pins for attachment thereof to the skull of a patient; a vest to be worn by the patient; superstructure means attached to the vest for generally supporting the halo ring thereabove; and adjustable two poster alignment means for securing the halo ring attached to a patient's skull in a desired alignment relative the superstructure means with the vest worn by the patient. In such an arrangement, a therapeutic skeletal process alignment is achieved for the articular patient with which the appliance is sued.

In the foregoing embodiment, the alignment means preferably includes a pair of support rods and four respective clamp means. A first pair of the clamp means are directly associated with the superstructure means for selectively clamping respective lower ends of the support rods. A second pair of the clamp means are directly associated with the halo ring for selectively clamping respective upper ends of the support rods in a selected slidably adjusted position thereof.

Another present exemplary embodiment concerns an orthopedic appliance to be worn by a patient, comprising a patient vest, a patient halo ring, a pair of clamps and corresponding clamp screws, and a pair of halo ring support posters. The patient vest preferably includes poster mounting means supported thereon, while the patient halo ring is provided with a plurality of threaded holes formed in the periphery thereof and a plurality of skull pin screws received respectively in selected of such holes.

In the foregoing embodiment, the clamps are respectively rotatably supported on generally opposite lateral sides of the patent halo ring by receipt of the corresponding clamp screw in selected of the patient halo ring threaded holes. At the same time, each of the clamps respectively define a poster receipt channel for slidable receipt of a support poster therein, which channel is tightened by its respective clamp screw. With the foregoing halo ring support posters, each such poster is supported at a lower end thereof by the poster mounting means, while such poster is slidably supported generally at an upper end thereof in the poster receipt channel of a respective one of the clamps. With such an arrangement, tightening of a clamp screw simultaneously fixes the selected slidably adjusted position of a support poster relative its corresponding clamp and fixes the selected rotatably adjusted position of the clamp relative the halo ring, so as to readily adjust and secure a selected patient skeletal process alignment simply by tightening of the respective clamp screws.

The present invention also concerns various embodiments of an orthopedic treatment process or methodology for a patient relating to use of an adjustable, two poster halo system orthopedic appliance, such as the exemplary embodiments described above. In one such exemplary process, the halo ring and vest are applied to the patient; the first pair of clamp means are loosely affixed relative the vest and the second pair of clamp means are loosely affixed to the halo ring; the support rods are loosely inserted into the respective clamp means therefor, with the rods in slidably adjustable relationship at least with the second pair of such clamp means (i.e., the clamps associated with the halo ring); the patient's skeletal process is thereafter aligned in desired orientation; and then the support rods are clamped with the four respective clamp means for securing the halo ring relative the vest. With such process, a therapeutic skeletal process alignment is achieved.

Those of ordinary skill in the art will better appreciate the features and aspects of such embodiments, methods, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures in which:

FIG. 4 illustrates a patient in a supine position, during application of an exemplary embodiment in accordance with this invention, in accordance with present methodology;

FIGS. 5, 6, and 7 are generally side perspective views of an exemplary present halo ring and adjustable two poster alignment means in accordance with the present invention, during application and adjustment thereof in accordance with present methodology.

Figure 1:
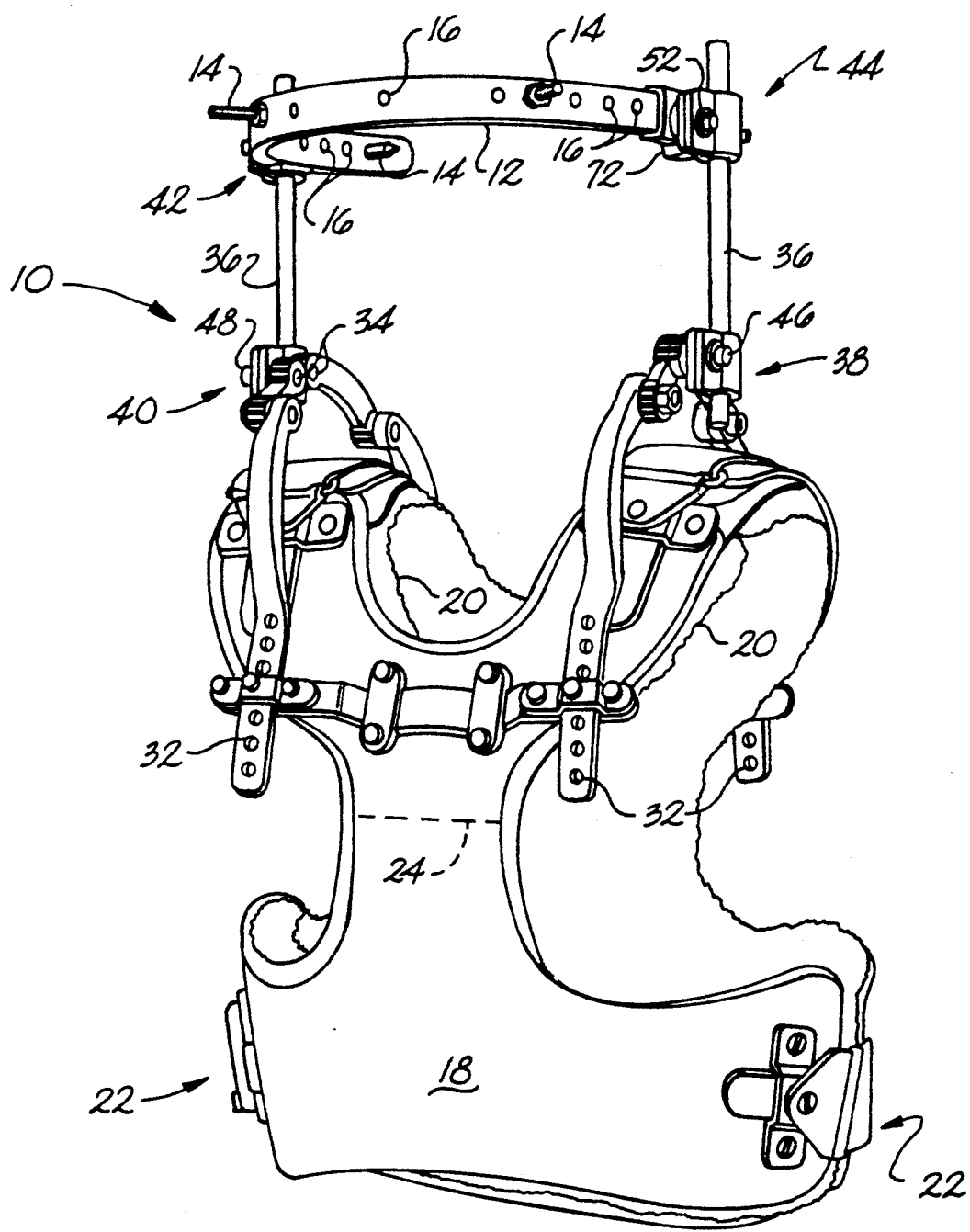
FIG. 1 is a perspective view of an exemplary embodiment of the present invention as fully assembled (but not applied to a patient)

Repeat use of reference characters throughout the present specification and appended drawings is intended to represent same or analogous features, elements, or steps of the invention.

DETAILED DESCRIPTION OF THE PREFERRED EMBODIMENTS

Figure 2:
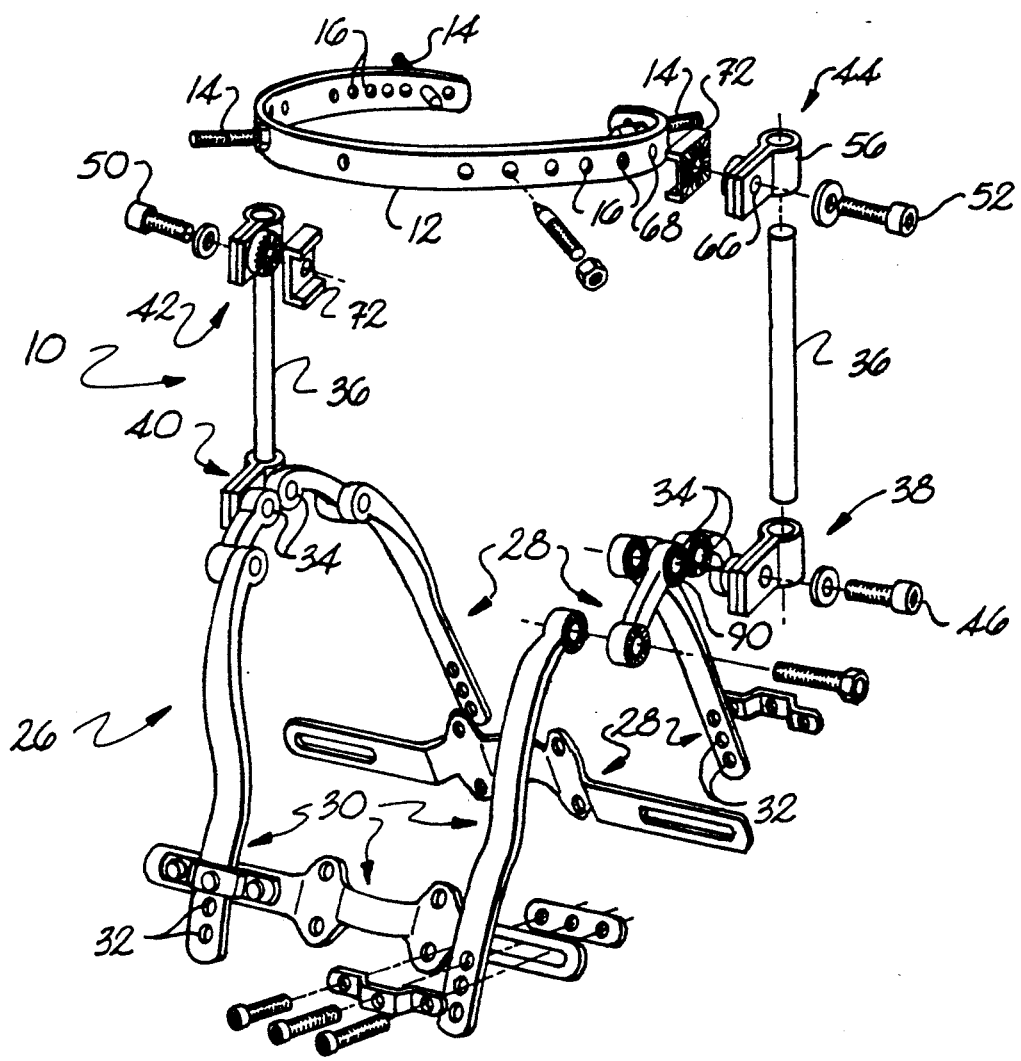
FIG. 2 is an exploded, perspective view of various features of the present exemplary embodiment of application FIG. 1.
Figure 3:
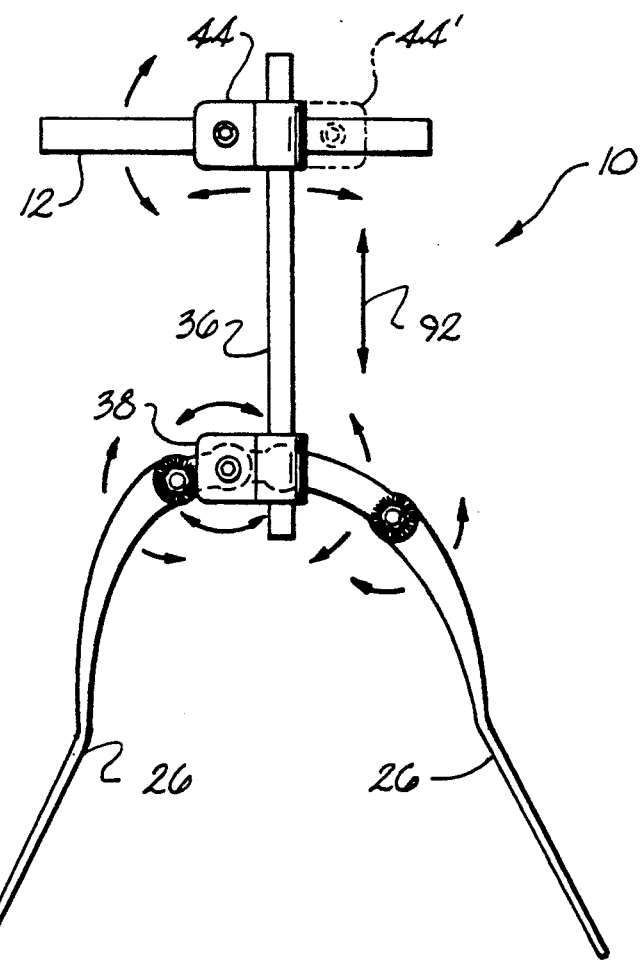
FIG. 3 is a side elevational view of various features illustrated in present FIG. 2, and further illustrating certain adjustability features of the present invention.

Those of ordinary skill in the art will appreciate that the present invention is not solely limited to practice of the present exemplary embodiments. Such present embodiments (both apparatus and methodology) are presented simply for illustration and explanation of the subject invention. For example, present FIGS. 1 through 3 illustrate respectively an assembled perspective view, an exploded perspective view, and a side elevational view of a present exemplary adjustable, two poster halo system orthopedic appliance generally 10 in accordance with this invention. Such an appliance includes a halo ring 12 which carries a plurality of skull pins 14 for attaching ring 12 to the skull of patient in a conventional manner as understood by those of ordinary skill in the art. Such threaded skull pins 14 are received in selected of the plurality of threaded holes 16 spaced about the periphery of halo ring 12.

FIG. 1 illustrates a vest 18 which may be formed of plastic type material and fitted to the chest of a patient as understood by those of ordinary skill in the art. A fleece lining 20 or the like may be used for added patient comfort. The various straps 22 and living hinge feature 24 are conventional and need not be discussed in detail for complete understanding of the present invention.

So as to more fully and clearly illustrate the present invention, present FIGS. 2 and 3 illustrate in exploded perspective view and side elevational view, respectively, superstructure means (generally 26) which attach to the vest 18 for generally supporting halo ring 12 thereabove. As illustrated, a portion 28 of such superstructure means attaches to the posterior (i.e.. rear) of vest 18 while other portions (generally 30) of the superstructure means attach to the anterior (i.e., front) of vest 18. Of course, different superstructure arrangements may be practice within the scope of this invention, and various features for adjustability of the superstructure may be provided or omitted, as desired for specific situations. For example, a plurality of adjustment holes 32 may be provided in conjunction with adjusting the height of such superstructure relative the vest. Additional discussion and explanation of such features is not required for a complete understanding of the present invention, but will be completely understood by one of ordinary skill in the art from the present FIGS. 1 through 3.

Superstructure means 26 provides threaded mounting holes such as 34 (see FIG. 2) by which clamp features in accordance with the present invention may be associated with vest 18 for supporting the lower ends of a pair of support rods or posts 36. Only one of such posts is visible in the side elevational view of FIG. 3. Alternatively, superstructure 26 may be provided with a single of such threaded holes 34 on each lateral side thereof.

The pair of support rods 36 are in accordance with this invention preferably associated with four respective clamp means 38, 40, 42, and 44. While different clamp means arrangements may be practiced, it is preferred generally that clamps 38 and 40 be identical, and comprise a first pair of clamp means directly associated with the superstructure means for selectively clamping respective lower ends of the support rods 36, while clamps 42 and 44 are identical to one another and comprise a second pair of clamp means directly associated with halo ring 12 for selectively clamping respective upper ends of the support rods 36. It is further preferred that at least such second pair of clamps 42 and 44 support rods 36 in selected slidably adjusted positions thereof, as discussed hereinbelow. In further embodiments of the subject invention, it is likewise preferred that the first pair of clamps 38 and 40 selectively clamp respective rod lower ends in selectively slidably adjusted positions thereof.

Each of the clamps 38, 40, 42, and 44 have a corresponding single clamp screw, screws 46, 48, 50, and 52. In embodiments intended to be MRI compatible, it is preferred that such bolts comprise nonmagnetic alloys, such as titanium. It is further preferred that such clamp screws comprise threaded screws with socket cap style drive heads, as illustrated. Such an arrangement permits advantageous use of a convention T-shaped handle socket drive, which further facilitates rapid application and adjustment of the subject appliance in accordance with the present invention.

Figure 8:
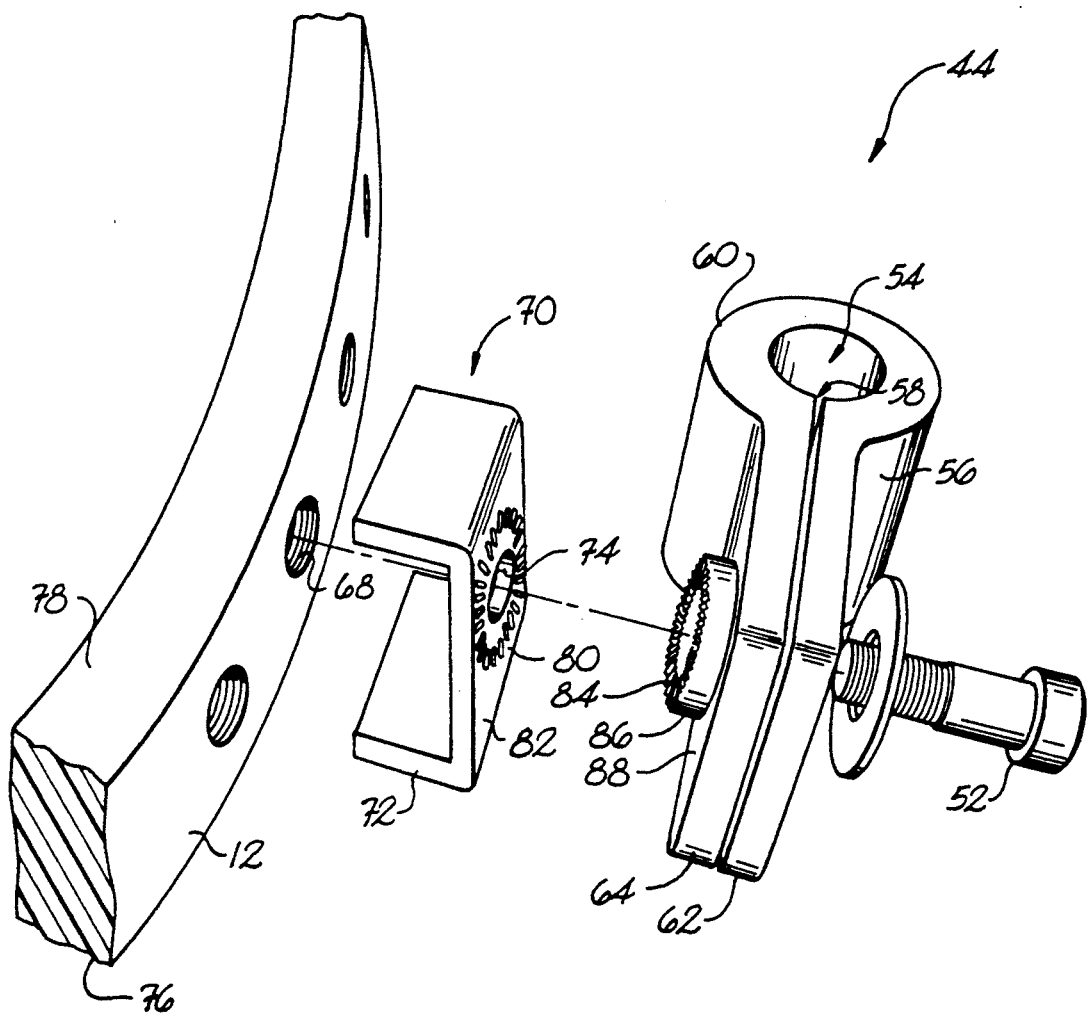
FIG. 8 is an enlarged exploded, perspective view of certain present clamping features in association with an exemplary halo ring.

Present FIG. 8 illustrates an enlarged, exploded perspective view of exemplary clamp means 44, which as shown in present FIGS. 1 and 2 is generally associated with halo ring 12 for selectively clamping the generally upper end of support poster 36 located on the patient's left lateral side. As represented in the figures, clamp means 44 defines a poster receipt channel 54 for slidable receipt of a poster 36 therein, which channel is tightened by tightening of the respective clamp screw 52.

More specifically in accordance with the present invention, clamp means 44 includes a locking element 56, with the poster receipt channel 54 thereof formed as a generally cylindrical channel therein for slidably receiving one of the support rods 36. Locking element 56 further includes a slit 58 formed longitudinally and radially through such locking element between its outside diameter 60 and channel 54 thereof. A pair of opposing wing members 62 and 64 extend from locking element 56 on respective sides of such slit 58 thereof with such wing members having aligned screw holes 66 (FIG. 2) therein. The clamp means 44 includes its respective single clamp screw 52, which is adapted to be received in the wing member screw holes 66 and threadably received in a threaded hole 68 of halo ring 12.

While FIG. 2 illustrates such clamp means arrangement in exploded view (as in FIG. 8), FIG. 1 illustrates an assembled view of such a clamp means arrangement. As will be apparent to those of ordinary skill in the art, tightening of clamp screw 52 simultaneously fixes a rotatably adjusted position of clamp means 44 relative the appliance and draws the wing members 62 and 64 thereof together so as to fix the slidably adjusted position of the support rod received in channel 54. Alternate clamp means and post arrangements may be practiced. For example, post and corresponding channel shapes need not be cylindrical only; rectangular or other shapes may suffice for given embodiments.

As should be further apparent to those of ordinary skill in the art, the remaining present exemplary clamp means 38, 40, and 42 preferably share such features with exemplary clamp 44. While in general clamp means 42 will be identical to that of clamp means 44, the first pair of clamp means 38 and 40 may omit certain features hereinafter discussed with respect to the second pair of clamp means 42 and 44. As understood from the figures, the respective clamp screws 46 and 48 of the first pair of clamp means 38 and 40 are received in the threaded holes 34 of the superstructure means 26, in a fashion similar to which screw 52 is received in threaded hole 68 as in present FIG. 8. In such instance, tightening of one or both of the clamp screws 46 and 48 results in fixing the respective clamp means 38 and 40 relative superstructure means 26, while fixing the slidably adjusted position of the support rod lower ends relative such clamp means.

An additional feature illustrated in present FIG. 8 which is shared by the second pair of clamp means 42 and 44, but generally not used in association with clamp means 38 and 40, includes a halo ring serration adapter means 70, which is operative for strengthening the respective clamping effect between halo ring 12 and clamp means 44. More particularly, such halo ring serration adapter means includes a U-shaped bracket 72 which is adapted to be carried on the halo ring 12 between such ring and a wing member 64 of clamp 44. Such bracket 72 further includes a screw hole 74 which is to be aligned with the threaded screw hole 68 of halo ring 12. Since the extended portions of U-shaped bracket 72 engage a lower side 76 and upper side 78 of halo ring 12, bracket 72 helps to provide greater stability and strength to the clamping effect created with clamp means 44.

Further contributing to enhanced clamping effect is the use of serrations 80 formed on the face 82 of bracket 72 which oppositely faces serrations 84 formed on a face of wing member 64. Preferably, serrations 84 are mounted on or formed in an integral boss 86 extending from face 88 of wing member 64. However, other arrangements may be practiced. For example, in connection with clamp means 38 and 40, serrations 90 may be provided directly about threaded hole 34 for engaging and contacting serrations similar to those as shown by reference character 84 in present FIG. 8.

Those of ordinary skill in the art will appreciate from the foregoing discussion in conjunction with FIGS. 1 through 3 and 8 that an orthopedic appliance in accordance with the subject invention advantageously permits application and adjustment of such present device with a minimum of effort and with maximum time efficiency. For example, in each instance, tightening of one of the four clamp screws 46, 48, 50, and 52, results in the corresponding clamp associated with such clamp screw becoming fixed in a rotatably selected position relative either halo ring 12 or superstructure means 26, while simultaneously fixing a slidably selected position of a support rod 36 relative thereto. In such manner multiple-axes securements are simultaneously effected with tightening of a single screw. Conversely, multi-axes adjustments are permitted by the untightening of a single clamp screw.

Such adjustment features of the present invention are further illustrated by the several double headed arrows (both curved and straight) in present FIG. 3. For example, double headed arrow 92 represents potential movement of support poster 36 along an axial direction thereof whenever exemplary clamp means 38 and 44 are loosely fitted or associated therewith. Likewise, the various curved arrows illustrated in a number of areas of FIG. 3 represent pivotable movements of which appliance 10 is capable whenever clamp means 38 and 44 are only loosely fitted, i.e., respective clamp screws 46 and 52 thereof are not fully tightened. It should be understood that the other poster 36 and clamp means 40 and 42 are not illustrated in the view of FIG. 3, but are similarly actuated in so far as appliance operations are concerned. Dotted line representation of clamp means 44' also represents pivotable movement of the subject invention resulting in fact in an alternate location of clamp means 44 relative the remaining structure of appliance 10. In such alternate location, clamp means 44 in effect is associated with a different threaded hole of halo ring 12.

Those of ordinary skill in the art will appreciate that the various adjustments discussed above with respect to appliance 10 may be used in conjunction with the various manipulations practiced for achieving a desired orientation of a patient's cervical spine, including the degree of traction applied thereto. Accordingly, discussion of such aspects of application and use of the present halo-vest system is not required for complete understanding of the present invention. However, the following discusses advantageous methodology which may be practiced in accordance with the invention, including the use of the present exemplary embodiment discussed herewith.

More specifically, present FIGS. 4 through 7 represent certain aspects of present methodology primarily involving application of an orthopedic appliance 10 in accordance with this invention to a patient primarily situated in a supine position. In FIG. 4, an exemplary patient generally 100 is shown as situated in a supine position on a mattress or other support 102. Patient 100 is shown after having received application of halo ring 12, generally secured to the patient's skull or head 104 with skull pins 14, and after having received vest 18 and exemplary superstructure means 26.

The details of fitting ring 12 to the patient's skull are not critical to a present understanding of the subject invention, and may include steps well known to those of ordinary skill in the art and as already conventionally practiced in the prior art. In general, preferably four skull pins are used at spaced intervals about the periphery of the skull, and application of halo ring 12 is performed in conjunction with at least initial spinal alignment and head alignment of the patient. It will already be appreciated by those of ordinary skill in the art that various conventionally available halo ring positioning devices may be practiced in conjunction with application of a present appliance 10, and in conjunction with practice of the overall present methodology. Similarly, the posterior and anterior portions of vest 18 may be applied in conventional steps, and the superstructure means 26 correspondingly outfitted to the vest.

After application of halo ring 12 and vest 18 to patient 100, present methodology making use of the present exemplary orthopedic appliance may continue with loose affixation of the various clamp features. More specifically, clamp means in accordance with the present invention, such as exemplary clamps 38, 40, 42, and 44, may be loosely affixed relative vest 18 and halo ring 12. In the specific illustrated exemplary embodiment, such loose affixation means generally that the respective clamp screws 46, 48, 50, and 52 may be threadably matted into their respected threaded holes, but not completely tightened. In such condition, the locking elements and opposing wing members of the clamps remain freely rotatable relative their respective support bases, but are supported overall. More specifically, the first pair of clamp means 38 and 40 are loosely affixed and supported relative the vest 18, at least in the sense that they are supported on superstructure means 26 as illustrated in present FIG. 4, while the second pair of clamp means 42 and 44 are loosely affixed to halo ring 12, as also illustrated.

Figure 5:
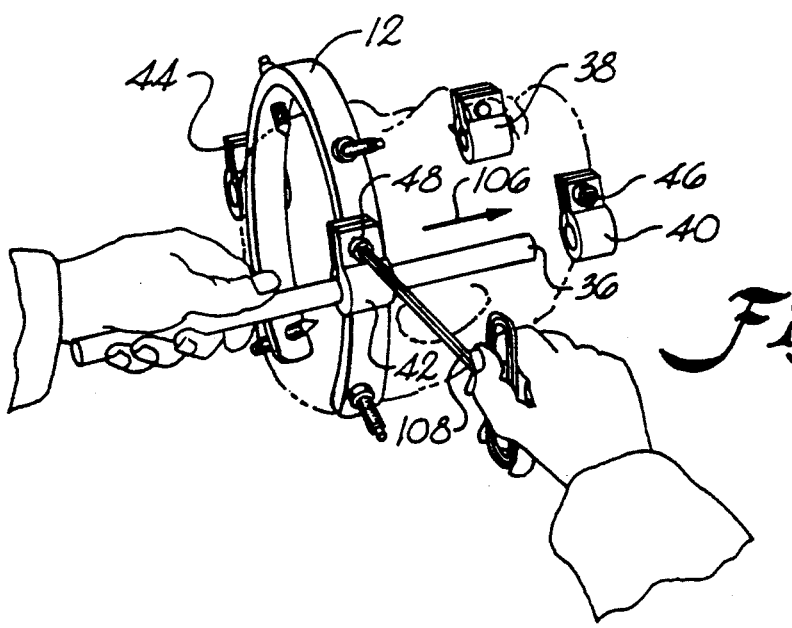

Present FIGS. 5 through 7 more specifically illustrate remaining features of the present methodology. With the skeletal process alignment of the patient otherwise generally achieved as desired, a support rod or poster 36 may simply slide through the support poster receipt channels of the respective clamp means, such as in the exemplary direction 106 as illustrated in present FIG. 5. As represented, the clamp screws 48 and 46 are adequately loosened, such as with an exemplary T-shaped handle socket drive 108 so as to permit poster 36 to slide through the respective receipt channels. Once the poster is seated in the desired position, and once the patient is properly and fully aligned in a desired orientation, the respective clamps 40 and 42 may be used to selectively clamp the respective lower end and upper end of poster 36. As will be understood by those of ordinary skill in the art, such clamping is achieved simply by tightening of the respective clamp screws 46 and 48, which draw the respective wing members of such clamps 40 and 42 together, while at the same time securing such clamps respectively to the superstructure means (not illustrated in present FIG. 5) and the halo ring 12.

As further represented in present FIGS. 6 and 7, the second of the pair of support posters 36 may likewise be slidably introduced and properly positioned for securement by clamps 38 and 40 at the respective lower and upper ends thereof. Once again, advantageously in accordance with the present invention, the second poster 36 may be secured quickly and simply by complete tightening of the respective clamp screws for clamp means 38 and 44.

Several differences between present FIGS. 6 and 7 illustrate certain other features of the present methodology. For example, present FIG. 6 illustrates essentially nonparallel alignment of the respective support posters 36. Using the respective four clamps 38, 40, 42, and 44, a patient may be secured in such an alignment, or on the other hand, such twisting or turning may be used for temporary or intermediate placement of the patient. For example, the present invention very simply permits torquing or twisting of the patient's neck relative the longitudinal axis thereof, essentially by selected pivoting of the upper ends 110 of posters 36 as illustrated in present FIG. 6. In other words, the health specialist applying the orthopedic appliance 10 to a patient could stand at the head of the patient and manipulate ends 110 for readily introducing a desired temporary or permanent torqued orientation of the patient's skeletal process. Present FIG. 7 represents a typical alignment wherein posters 36 are substantially parallel, and wherein the degree of traction introduced to the patient's skeletal process is defined by the amount of separation between respective lower end and upper end pairs of clamp members 38, 40, and 42, 44.

FIG. 7 further represents generally another feature of the subject invention (both apparatus and method) relating to an additional clamp or rod lock means 112 which may be optionally practiced. In particular, additional rod clamp means 112 may comprise a mechanism similar to member 56 of present FIG. 8, and which may be fitted onto poster 36 between respective clamps 40 and 42. Thereafter, such additional poster clamp means 112 may be slidably positioned adjacent one of such clamps, and clamp screw 114 thereof afterwards locked. Such additional means serve to further secure the position of poster 36 relative the remainder of the structure, for added confidence in the stability and strength of the overall assembly.

Present FIG. 8 further represents additional aspects of the present methodology. For example, present FIG. 8 represents to those of ordinary skill in the art the specific additional preferred step with respect to application of clamp means 42 and 44, in that the adapter bracket 72, if used, must be added to and carried on halo ring 12 prior to introduction of the clamp screw.

It should be further understood by those of ordinary skill in the art that the foregoing presently preferred embodiments are exemplary only, and the attendant description thereof is likewise by way of words of example, rather than words of limitation. Accordingly, their use does not preclude inclusion of such modifications, variations, and/or additions to the present invention as would be readily apparent to those of ordinary skill in the art. For example, certain steps of the present method may be modified within the spirit and scope of the present invention. For example, both posters may be introduced and aligned prior to securement of either poster, or the left or right poster may be introduced and secured in advance of the other poster. Likewise, it is within the spirit and scope of the present invention that the present methodology and appliance features may be used in conjunction with an appliance already worn by a patient. In such instances, the advantages of rapid adjustability with minimum operating steps would be of considerable importance. In other words, once a present appliance is being worn by a patient, any necessary alignment or traction adjustments (for whatever reason) could be made conveniently, rapidly, and accurately.

It should be further apparent to those of ordinary skill in the art that the above exemplary appliance and methodology embodiments achieve present objects, such as minimizing the amount of time necessary to apply and/or adjust the appliance, or such as achieving a highly stable and secure alignment with minimum appliance bulk.

It will be likewise understood by those of ordinary skill in the art that the various metal elements of a present exemplary apparatus may be provided in nonmagnetic alloy materials, such as titanium, so as to render the subject appliance compatible with MRI or other imagery techniques. For example, the poster, superstructure means, and halo ring may be composed of composite materials, such as carbon fibers, particularly mixtures of graphite and nylon, all of which further in combination with the non-magnetic alloy materials may result in artifact-free image quality MRI. Of course, other equivalent materials may be used for such purposes, or other materials may be used for different purposes.

Likewise, it would be understood to those of ordinary skill in the art that different size vests and halo rings may be provided in accordance with the present invention, so as to accommodate different patients, such as either children or adults. All such variations, and others, such as the material or formation of the patient vest, are intended to come within the spirit and scope of the present invention, by virtue of present reference thereto, the scope of such present invention being set forth more particularly in the appended claims.

What is claimed is:

1. An adjustable, two poster halo system orthopedic appliance, comprising:
   a halo ring carrying a plurality of skull pins for attachment thereof to the skull of a patient;
   a vest to be worn by the patient;
   superstructure means attached to the vest for generally supporting said halo ring thereabove; and
   adjustable two poster alignment means for securing said halo ring attached to a patient's skull in a desired alignment in multiple axes relative said superstructure means with said vest alignment is achieved for the particular patient with which the appliance is used;
   wherein said adjustable alignment means includes a pair of support rods and four respective clamp means, with a first pair of said clamp means directly associated with said superstructure means for selectively clamping respective lower ends of said support rods with a desired axial relationship between said support rods and said superstructure means, and with a second pair of said clamp means directly associated with said halo ring for selectively clamping respective upper ends of said support rods in a selected slidably adjusted position thereof and for selectively clamping said second pair of clamp means in a rotatably selected position relative said halo ring.

2. An adjustable, two poster halo system orthopedic appliance as in claim 1, wherein said first pair of said clamp means selectively clamp respective rod lower ends in selected slidably adjusted positions thereof.

3. An adjustable, two poster hal system orthopedic appliance as in claim 2, wherein each of said clamp means includes a locking element having a generally cylindrical channel therein for slidably receiving one of said support rods, a slit formed longitudinally and radially through said locking element between its outside diameter and said channel, and a pair of opposing wing members extending from said locking element on respective sides of said slit, with said wing members having aligned screw holes therein, and wherein said respective clamp means each further include a single clamp screw received in said wing member screw holes and threadably received in one of said superstructure means and said halo ring, so that tightening of each clamp screw simultaneously fixes the rotatably adjusted position of the corresponding clamp means relative said appliance and draws said wing members thereof together so as to fix the slidably adjusted position of the corresponding support rod.

4. An adjustable, two poster halo system orthopedic appliance as in claim 3, wherein opposing faces of said superstructure means and of wing members of said first pair of said clamp means include serrations so as to strengthen the respective clamping effect between said superstructure means and said first pair of said clamp means.

5. An adjustable, two poster halo system orthopedic appliance as in claim 3, wherein each of said second pair of said clamp means further includes halo ring serration adapter means for strengthening the respective clamping effect between said halo ring and said second pair of said clamp means.

6. An adjustable, two poster halo system orthopedic appliance as in claim 5, wherein said halo ring serration adapter means includes a U-shaped bracket carried on said halo ring between said ring and a wing member of one of said clamp means locking elements, said bracket having a screw hole aligned with a screw hole of said halo ring, and wherein said appliance further includes serrations formed on opposing faces of said bracket and a wing member of an adjacent locking element.

7. An adjustable, two poster halo system orthopedic appliance as in claim 1, wherein said halo ring, said superstructure means, and said alignment means are comprised of nonmagnetic alloys and of composite materials so that said orthopedic appliance may be used to produce artifact-free image quality MRI.

8. An orthopedic appliance to be worn by a patient, comprising:
   a patient vest with poster mounting means supported thereon;
   a patient halo ring with a plurality of threaded holes formed in the periphery thereof and a plurality of skull pin screws received respectively in selected of said holes;
   a pair of clamps and corresponding clamp screws, said clamps being respectively rotatably supported on generally opposite lateral sides of said patient halo ring by receipt of the corresponding clamp screw in selected of said patient halo ring threaded holes, and each of said clamps respectively defining a poster receipt therein, which channel is tightened by its respective clamp screw; and
   a pair of halo ring support posters, each such poster being supported at a lower end thereof by said poster mounting means and generally at an upper end thereof slidably supported in said poster receipt channel of a respective one of said clamps, so that tightening of a clamp screw simultaneously fixes the selected slidably adjusted position of a support poster relative its corresponding clamp and fixes the selected rotatably adjusted position of such clamp relative said halo ring, so as to readily adjust and secure a selected patient skeletal process alignment simply by tightening of said respective clamp screws.

9. An orthopedic appliance as in claim 8, further including:
   superstructure means attached to said patient vest for supporting said poster mounting means thereon; and
   wherein said poster mounting means includes a pair of support poster clamping elements each respectively secured to said superstructure means by a single securement element associated therewith such that tightening of one of such securement elements simultaneously draws its corresponding clamping element tight about its corresponding support poster so as to fix the slidable position of such poster while fixing the rotatable position of such clamping element relative said superstructure means.

10. An orthopedic appliance as in claim 9, wherein each of said securement elements comprises a nonmagnetic alloy screw with a socket cap drive head, and said poster mounting means and said poster clamping elements include frictional engagement means for enhanced clamping effect therebetween whenever the corresponding screw is tightened.

11. An orthopedic appliance as in claim 8, wherein said clamp screws and said skull pin screws comprise non-magnetic alloy materials, and said patient halo ring, said pair of clamps, and said pair of halo ring support posters comprise composite materials, for artifact-free image quality MRI performance of said orthopedic appliance.

12. An orthopedic appliance as in claim 8, further including a U-shaped adapter bracket carried on said halo ring between one of said threaded holes thereof and one of said clamps supported thereat, said bracket and said clamp including frictional engagement means for enhanced clamping effect therebetween whenever the corresponding clamp screw is tightened.

13. An orthopedic appliance as in claim 12, wherein said frictional engagement means includes serrations carried on respective opposing faces of said bracket and said clamp so that such serrations are brought into mutual frictional engagement whenever the corresponding clamp screw is tightened.

14. An orthopedic appliance as in claim 8, further including poster clamping lock means carried on said respective support posters for locking the position of said respective support posters relative said appliance.

15. An orthopedic treatment process for a patient, including use of an adjustable, two poster halo system orthopedic appliance, said process comprising:

providing a halo ring carrying a plurality of skull pins for attachment thereof to the skull of a patient; a vest to be worn by the patient; and adjustable two poster alignment means for securing said halo ring when attached to a patient's skull in a desired alignment in multiple axes relative said vest when worn by the patient, said adjustable alignment means including a pair of support rods and four respective clamp means, with a first pair of said clamp means associated with said vest for selectively clamping respective lower ends of said support rods with a desired axial relationship between said support rods and said superstructure means, and with a second pair of said clamp means directly associated with said halo ring for selectively clamping respective upper ends of said support rods in a selected slidably adjusted position thereof and for selectively clamping said second pair of clamp means in a rotatably selected position relative said halo ring;

applying the halo ring and the vest to the patient;

loosely affixing said first pair of said clamp means relative said vest and said second pair of said clamp means to said halo ring;

loosely inserting said support rods into said respective clamp means therefor, with said rods in slidably adjustable relationship at least with said second pair of said clamp means;

aligning the patient's skeletal process in desired orientation; and thereafter operating said alignment means for securing said halo ring relative said vest by clamping said support rods with all four of said clamp means, so that a therapeutic skeletal process alignment is achieved for the patient with which the appliance is used.

16. An orthopedic treatment process as in claim 15, wherein said loosely inserting step includes providing said first pair of said clamp means so as to selectively clamp respective rod lower ends in selected slidably adjusted positions thereof.

17. An orthopedic treatment process as in claim 16, wherein each of said clamp means are provided so as to include a locking element having a generally cylindrical channel therein for slidably receiving one of said support rods, a slit formed longitudinally and radially through said locking element between its outside diameter and said channel, and a pair of opposing wing members extending from said locking element on respective sides of said slit, with said wing members having aligned screw holes therein, and wherein said respective clamp means each further are provided so as to include a single clamp screw received in said wing member screw holes and threadably received in one of said superstructure means and said halo ring, and wherein each clamp screw so as to simultaneously fix the rotatably adjusted position of the corresponding clamp means relative said appliance and draw said wing members thereof together so as to fix the slidably adjusted position of the corresponding support rod.

18. An orthopedic treatment process as in claim 17, further including providing opposing faces of said vest to which said clamp means attach and of wing members of said first pair of said clamp means with serrations so as to strengthen the respective clamping effect between such opposing faces.

19. An orthopedic treatment process as in claim 17, further including providing each of said second pair of said clamp means with halo ring serration adapter means for strengthening the respective clamping effect between said halo ring and said second pair of said clamp means.

20. An orthopedic treatment process as in claim 19, wherein providing said halo ring serration adapter means includes providing a U-shaped bracket carried on said halo ring between said ring and a wing member of one of said clamp means locking elements, said bracket having a screw hole aligned with a screw hole of said halo ring, and further includes providing serrations formed on opposing faces of said bracket and a wing member of an adjacent locking element.

21. An orthopedic treatment process as in claim 15, wherein providing said halo ring, said superstructure means, and said alignment means includes forming such members of nonmagnetic alloys and of composite materials so that said orthopedic appliance may be used to produce artifact-free image quality MRI.

22. A method of applying an orthopedic halo system to be worn by a patient, said method comprising:

providing a patient halo ring with a plurality of threaded holes formed in the periphery thereof and securing such ring to the patient's skull using a plurality of skull pin screws received respectively in selected of said threaded holes;

applying to the patient a patient vest with poster mounting means supported thereon;

providing a pair of clamps and corresponding clamp screws, and respectively rotatably supporting said clamps on generally opposite lateral sides of said patient halo ring by respective receipt of the corresponding clamp screws in selected of said patient halo ring threaded holes, each of said clamps respectively defining a poster receipt channel for slidable receipt of a support poster therein, which channel can be tightened with tightening of its respective clamp screw; and providing a pair of halo ring support posters, and loosely supporting each such poster at a lower end thereof by said poster mounting means and generally slidably supporting such poster at an upper end thereof in said poster receipt channel of a respective one of said clamps;

aligning the patient's skeletal process in a desired orientation; and securing the respective poster lower ends with said poster mounting means, and tightening said clamp screws so as to simultaneously fix the selected slidably adjusted position of each support poster relative its corresponding clamp and fix the selected rotatably adjusted position of each clamp relative said halo ring, so as to readily adjust and secure a selected patient skeletal process alignment simply by securing said poster mounting means and tightening said respective clamp screws.

23. A method as in claim 22, further including:

providing superstructure means attached to said patient vest for supporting said poster mounting means thereon; and wherein applying said vest with said poster mounting means includes providing a pair of support poster clamping elements each respectively secured to said superstructure means by a single securement element associated therewith such that tightening of one of such securement elements simultaneously draws its corresponding clamping element tight about its corresponding support poster so as to fix the slidable position of such poster while fixing the rotatable position of such clamping element relative said superstructure means.

24. A method as in claim 23, wherein providing said securement elements includes providing a nonmagnetic alloy screw with a socket cap drive head, and said method further includes providing said poster mounting means and said poster clamping elements with frictional engagement means for enhanced clamping effect therebetween whenever the corresponding screw is tightened.

25. A method as in claim 22, further including providing said clamp screws and said skull pin screws comprised of nonmagnetic alloy materials, and providing said patient halo ring, said pair of clamps, and said pair of halo ring support posters comprised of composite materials, for artifact-free image quality MRI performance of said halo system.

26. A method as in claim 22, further including providing a U-shaped adapter bracket carried on said halo ring between one of said threaded holes thereof and one of said clamps supported thereat, with said bracket and said clamp including frictional engagement means for enhanced clamping effect therebetween whenever the corresponding clamp screw is tightened.

27. A method as in claim 26, wherein providing said frictional engagement means includes forming serrations carried on respective opposing faces of said bracket and said clamp so that such serrations are brought into mutual frictional engagement whenever the corresponding clamp screw is tightened.

28. A method as in claim 22, further including applying a locking collar to each of said support posters for locking the position of said support posters relative said halo system.

* * * * *

UNITED STATES PATENT AND TRADEMARK OFFICE
CERTIFICATE OF CORRECTION

PATENT NO. : 5,203,765
DATED : April 20, 1993
INVENTOR(S) : FRIDDLE, JR.

It is certified that error appears in the above-identified patent and that said Letters Patent is hereby corrected as shown below:

Column 3, line 6, change "methodol" to --methodology--.

In the claims:

Column 11, line 22, after "vest" insert --worn by the patient, so that a therapeutic skeletal process--.
Column 11, line 43, change "hal" to --halo--.
Column 12, line 36, after "receipt" insert --channel for slidable receipt of a support poster--.
Column 14, line 19, after "wherein" insert --said securing of said clamp means includes tightening of--.

Signed and Sealed this

Ninth Day of May, 1995

*Attest:*

BRUCE LEHMAN

*Attesting Officer*  *Commissioner of Patents and Trademarks*